United States Patent
Besesty et al.

(10) Patent No.: US 7,034,325 B2
(45) Date of Patent: Apr. 25, 2006

(54) DEVICE FOR MEASURING GAS CONCENTRATION HAVING DUAL EMITTER

(75) Inventors: Pascal Besesty, Vaulnavey le Haut (FR); Engin Molva, Grenoble (FR); Emanuel Hadji, Fontaine (FR)

(73) Assignee: Commissariat a l'Energie Atomique, Paris (FR)

( * ) Notice: Subject to any disclaimer, the term of this patent is extended or adjusted under 35 U.S.C. 154(b) by 230 days.

(21) Appl. No.: 10/250,317

(22) PCT Filed: Jan. 4, 2002

(86) PCT No.: PCT/FR02/00025

§ 371 (c)(1),
(2), (4) Date: Dec. 16, 2003

(87) PCT Pub. No.: WO02/061403

PCT Pub. Date: Aug. 8, 2002

(65) Prior Publication Data

US 2004/0108462 A1    Jun. 10, 2004

(30) Foreign Application Priority Data

Jan. 5, 2001  (FR)  .................................. 01 00132

(51) Int. Cl.
*G01N 15/06* (2006.01)
(52) U.S. Cl. .................................. 250/573; 250/222.2
(58) Field of Classification Search .................... None
See application file for complete search history.

(56) References Cited

U.S. PATENT DOCUMENTS 5,797,682 A * 8/1998 Kert et al. .................. 374/123

OTHER PUBLICATIONS

Y. Shimose et al, Remote Sensing of Methane Gas by Differential Absorption Measurement Using a Wavelength Tunable DFB LD, IEEE Photonics Technology Letter. vol. 3 No. 1. Jan. 1991.

(Continued)

*Primary Examiner*—Que T. Le
(74) *Attorney, Agent, or Firm*—Thelen Reid & Priest LLP

(57) ABSTRACT

A device for measuring the concentration of a gas contained in a cavity and for checking the operation of a catalytic element in an exhaust line in an automobile vehicle. A first emitter (E1) composed of an optical pumped micro-cavity and for which the emission spectrum is within the gas absorption band emits a first radiation that passes through the cavity. A second emitter emits a second radiation that passes through the cavity. A receptor measures the optical intensity (I) of the radiation that passed through the cavity.

14 Claims, 5 Drawing Sheets

OTHER PUBLICATIONS

Uehara et al, Remote Detection of Methane with a 1.66-μm diode laser, Feb. 20, 1992/ vol. 31, No. 6/ Applied Optics.

M.K. Perry et al, Efficient 3.3 μm light emitting diodes for detecting methane gas at room temperature, Electronics Letters, Nov. 1, 1994, vol. 3., No. 23.

W. Dobbelaere et al, InAsSb Light Emitting Diodes and Their Appl. To Infra-Red Gas Sensors.

Y. Mao et al, Efficient 4.2 μm Light Emitting Diodes for Detecting $Co_2$ at room temperature, Electronics Letters, Feb. 29, 1996, vol. 32 No. 5.

A. Krier et al, High Power 4.6 μm LEDs For CO detection Grown by LPE, Electronics Letters, Sep. 16, 1999, vol. 35 No. 19.

* cited by examiner

DEVICE FOR MEASURING GAS CONCENTRATION HAVING DUAL EMITTER

CROSS-REFERENCE TO RELATED APPLICATION

This application claims priority based on International Patent Application No. PCT/FR02/00025, entitled "Device for Measuring Gas Concentration" by Pascal Besesty, Engin Molva and Emanuel Hadji, which claims priority to French application no. 01/00132, filed on Jan. 5, 2001, and which was not published in English.

TECHNICAL FIELD AND PRIOR ART

This invention relates to a gas concentration measurement device.

The invention is applicable in different fields, for example such as the analysis of gaseous industrial waste, analysis of exhaust gas from automobile vehicles, control of pure air inlet in closed containments, control of smells, etc.

One particularly advantageous application of the device according to the invention in the automotive field is for checking correct operation of the catalytic element of the exhaust system of a vehicle.

Different optical gas detection devices are known in prior art. For example, there are devices using laser emission diodes, light emitting diodes (LEDs), and lamps.

The document "*Remote Sensing of Methane Gas by Differential Absorption Measurement Using a Wavelength Tunable DFB LD*" (Y. Shimose et al., IEEE photonics technology letters, vol. 3, No. 1, p. 86, January 1991) and the document "*Remote Detection of Methane with a 1.66 µm Diode Laser*" (K. Uehara et al., Applied Optics, vol. 31, No. 6, p. 809, February 1992) disclose devices making use of laser diodes.

This type of device uses complex electronic processing circuits that are expensive due to the use of diodes with a very low wavelength (typically of the order of 1.65 µm). Therefore, these devices are not suitable for use in fields of application for the general public, for example such as the automotive field.

Known devices that use light emitting diodes have the advantage that they work at longer wavelengths between 3 and 6 µm. However, due to the very broad spectral width of the radiation emitted by the diodes, interference filters have to be used that result in low emission efficiency in the usage area. Moreover, this type of interference filter is expensive. There are other disadvantages with the use of light emitting diodes. Thus, drifts in the radiation emitted by diodes due to temperature variations are high, and temperature compensation circuits have to be used. Similarly, the transmission of radiation emitted by diodes varies considerably and optical corrections are necessary.

The following documents disclose optical detection devices that use light emitting diodes:

"*Efficient 3.3 µm light emitting diodes for detecting methane gas at room temperature*", M. K. Parry et al., Electronics letters, vol. 30, No. 23, p. 1968, November 1994, "*InAsSb light emitting diodes and their applications to infrared gas sensors*", W. Dobbelaere et al., Electronics letters, vol. 29, No. 10, p. 890, May 1993, "*Efficient 4.2 µm light emitting diodes for detecting $CO_2$ at room temperature*", Y. Mao et al., Electronics letters, vol. 32, No. 5, p. 479, February 1996, "*High power 4.6 µm LEDs for CO detection grown by LPE*", A. Krier et al., Electronics letters, vol. 35, No. 19, p. 1665, Sept. 1999.

Lamps (hot filament) also have the advantage that they work in the 3 to 6 µm range. However, due to the very broad spectral width of the emitted radiation, it is also necessary to use interference filters. The emission efficiency is even lower than the emission efficiency of light emitting diodes. Furthermore, the emission also varies considerably and an optical correction has to be made. Furthermore, a mechanical chopper is necessary if signal processing requires amplitude modulation.

In summary, none of the emitters mentioned above are suitable for making a compact, inexpensive and easy to use detection device. Furthermore, none of these devices can be used for simultaneous detection of several different gases.

The invention does not have the disadvantages mentioned above.

PRESENTATION OF THE INVENTION

This invention relates to a device for measuring the gas concentration, comprising:

- a cavity containing at least one gas for which the concentration is to be measured,
- at least one first emitter composed of an optical microcavity pumped by optical pumping means and for which the emission spectrum is within the gas absorption band,
- at least one second emitter composed of an optical microcavity pumped by optical pumping means and for which the emission spectrum is outside the gas absorption band,
- reception means for measuring the optical intensity of a first radiation output from the first emitter and transmitted through the cavity, and the optical intensity of a second radiation output from the second emitter and transmitted through the cavity, and
- a processing circuit for measuring the gas concentration starting from the optical intensity of the first radiation and the optical intensity of the second radiation.

The cavity may be an open or closed cavity. An "open" cavity means a cavity that includes openings enabling gas to be entrained in a flux. A "closed" cavity means a cavity that does not include such openings.

The invention also relates to a device for checking operation of a catalytic element in an exhaust line in an automobile vehicle, characterized in that it comprises a device for measuring the gas concentration according to the invention.

BRIEF DESCRIPTION OF THE FIGURES

Other specific features and advantages of the invention will become clear after reading one preferred embodiment made with reference to the appended figures, wherein.

The same marks represent the same elements in all figures.

DETAILED PRESENTATION OF EMBODIMENTS OF THE INVENTION

Figure 1:
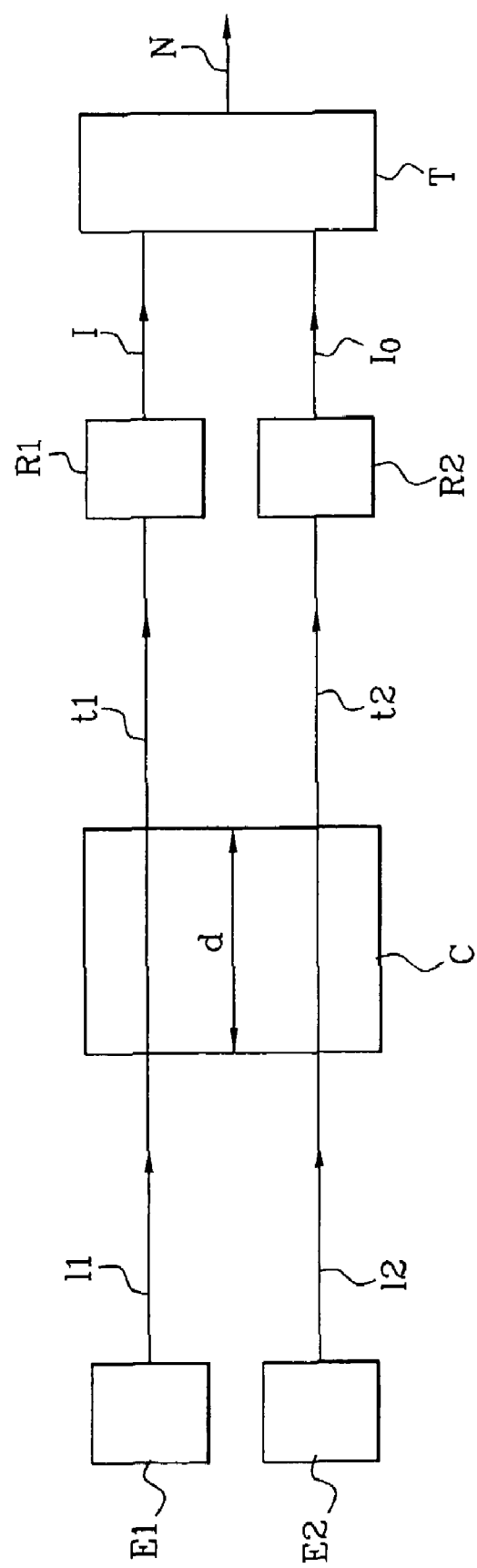
FIG. 1 shows a principle diagram for a device for measuring the gas concentration according to the invention.

FIG. 1 shows a principle diagram of a gas concentration measurement device according to the invention. The device comprises a cavity C containing a gas for which the concentration is to be measured, a first radiation emitter E1, a second radiation emitter E2, a first reception means R1, a second reception means R2, and an electronic processing circuit T.

The emission spectrum of the emitter E1 is within the absorption band of the gas to be detected whereas the emission spectrum of the emitter E2 is outside the absorption band of the gas to be detected. Radiation 11 and 12 emitted by emitters E1 and E2 respectively pass through the cavity C over a distance d to form detected radiation t1 and t2 respectively detected by reception means R1 and R2 respectively beyond the cavity. The reception means R1 outputs a measurement I of the optical intensity of the radiation t1 and the reception means R2 outputs a measurement $I_0$ of the optical intensity of the radiation t2. A processing circuit T outputs the measurement of the concentration N of the gas starting from measurements of the optical intensity I and $I_0$.

The result is:

$$\frac{I}{I_0} = \exp(-\alpha \times d)$$

where $\alpha = a \times N$, where a is the density of the gas in $m^{-1}$ $ppm^{-1}$, N is the gas concentration in ppm, where d is the length of the path of the optical beam in the gaseous medium as mentioned above.

We can then write:

$$\frac{I}{I_0} \approx 1 - \alpha \times d,$$

or $$\alpha \times d \approx 1 - \frac{I}{I_0},$$

and therefore $$\alpha \times d \approx \frac{\delta I}{I_0},$$

where $\delta I = I_0 - I$.

The conclusion is:

$$N = \frac{1}{a \times d} \times \frac{\delta I}{I_0}.$$

Each of the emitters E1 and E2 comprises a resonant optical micro-cavity in which the active region is a heterostructure with semiconductor that emits light at a wavelength determined by the choice of the semiconductor and the type of heterostructure. The active layer is made using the epitaxy technique with semiconducting materials such as for example CdHgTe, GaAlN, AlBN, GaAlAs, GaAsSb, GaAlSb, etc. or with different families of semiconducting alloys in the II–VI family (compounds of Cd, Zn, Hg, Mn, Mg with Se, S, Te), or the III–V family (Ga, Al, In, B with N, As, P, Sb).

In general, heterostructures are formed by stacking multilayers of alloys on a substrate. The active zone may comprise quantum wells that then form light emitting zones. Epitaxy is done using known "molecular beam epitaxy", "organometallic epitaxy", or "liquid phase epitaxy" type means.

In the micro-cavity emitter, the active zone made with semiconducting materials described above is located inside an optical micro-cavity composed of a Fabry-Perrot type cavity containing two mirrors. The Fabry-Perrot cavity is calculated so that optical resonance of the cavity corresponds to the emission wavelength of the semiconductor. The resonant optical micro-cavities (of the Fabry-Perrot type) are also known to experts in the subject.

The use of a resonant optical micro-cavity considerably improves the performances of the emitter compared with an emission without a resonant micro-cavity. The advantages related to use of a resonant micro-cavity are as follows:

improvement in the spontaneous emission and the emitted light quantity (increase by a factor equal to approximately 10), spectral refinement of the emission (the emission spectrum is refined by a factor of 10 to 20), better directivity (reduction in the divergence by an angle of about 20°), very large reduction in the dependence of the emission wavelength on temperature (reduction by a factor of 100).

Optical pumping necessitates a source with a wavelength less than the wavelength of the emitter so that it can be absorbed by the active zone of the semiconductor. For example, for infrared emitters based on CdHgTe emitting in the 3–5 µm range, a laser diode or a light emitting diode may be used, for example emitting at 780 nm, 800 nm or 980 nm. Advantageously, there is no need to regulate the emission wavelength of the optical pump. This very much simplifies the device, since there is no need for a temperature regulation.

The emission power is proportional to the power of the pump. For example, it may be between 1 and 100 microWatts at ambient temperature. For example, for the application considered here, we will use a laser diode to optically excite the emitters.

The input mirror to the optical micro-cavity is designed to be transparent to excitation wavelengths of the beam of the pump laser diode. This is made conventionally with a dichroic mirror, with a transparency band at excitation wavelengths and a high reflectivity at the wavelength of the emitter.

Figure 2:
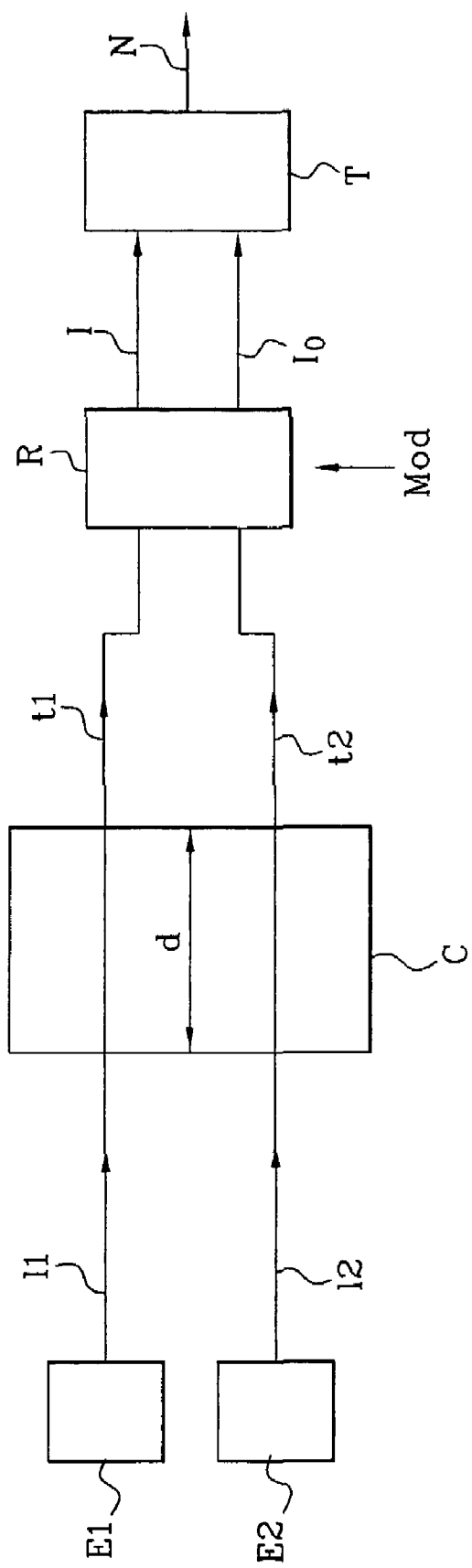
FIG. 2 shows a principle diagram of an improvement to the device for measuring the gas concentration shown in FIG. 1.

It is also possible to increase the sensitivity of the device by using dedicated electronics. The light intensity of emission beams from infrared emitters E1 and E2 can be varied by modulating the beam output from the optical pumping element. If it is considered that the pumping element is a laser diode, the optical output beam from the infrared emitter can be modulated with a frequency of more than 100 MHz. Electronic filter functions (possibly the synchronous detection function) can be controlled through this property, to select the useful signal to be detected (improvement of the signal to noise ratio). In general, each reception means comprises an interference filter to select light to be received. In the case of synchronous detection, it is then possible to eliminate this filter from the reception means. For example, by using encoded modulation, a single reception element can be selectively activated according to the activated emitter. This embodiment of the invention is shown in FIG. 2, in which an encoded modulation command Mod is applied to a single reception means R.

According to the invention, the fact of making a differential measurement between a useful signal measurement and a reference signal advantageously reduces ambient parasite noise and eliminates temperature drifts from measurement systems.

Figure 3:
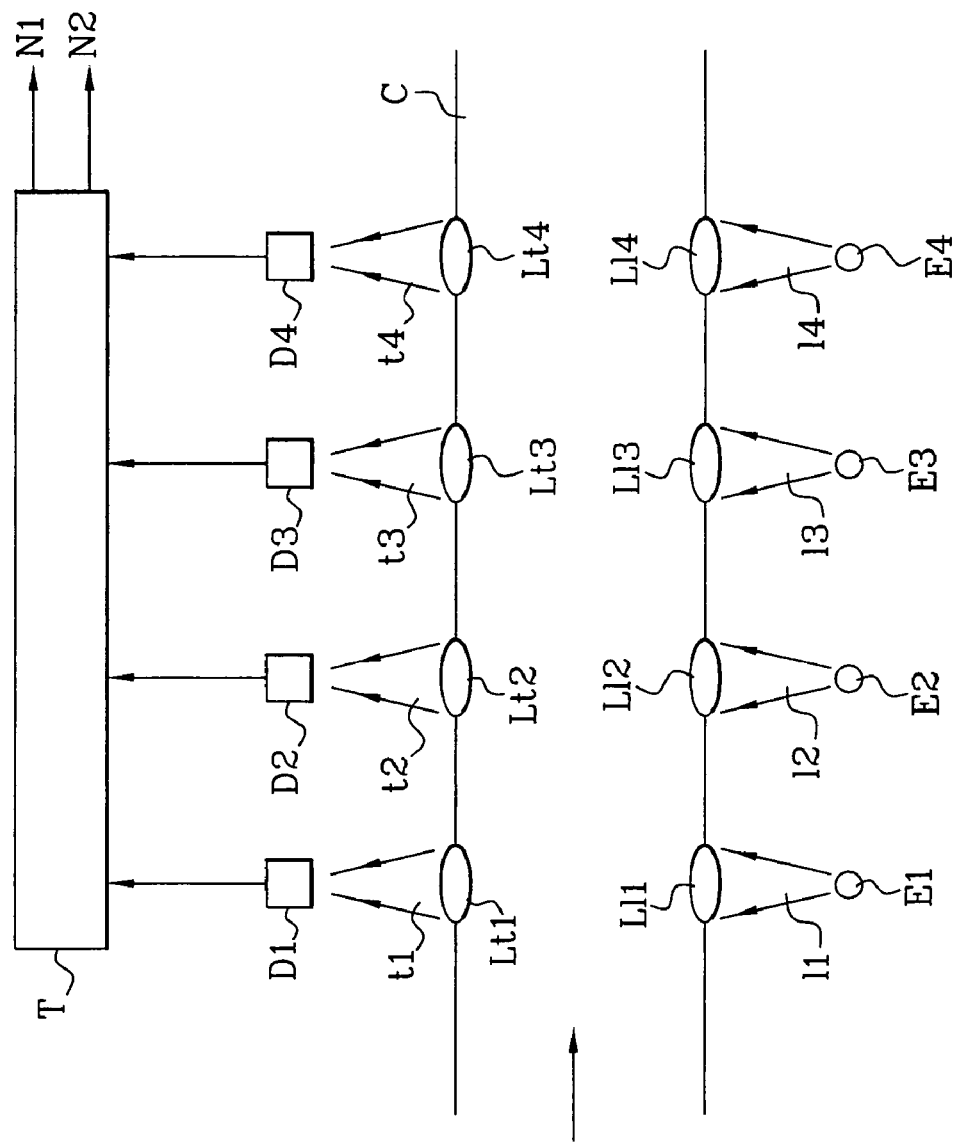
FIG. 3 shows a first example embodiment of a gas concentration measurement device according to the invention.

FIG. 3 shows a first example embodiment of the gas concentration measurement device according to the invention.

The device comprises four emitters E1, E2, E3, E4 and four detecting diodes D1, D2, D3, D4. Radiation li (i=1, 2, 3, 4) output from emitter Ei is coupled to the cavity C by a lens Lli. Radiation ti (i=1, 2, 3, 4) output from cavity C is coupled to detector Di by a lens Lti. The electrical signals output from detectors Di (i=1, 2, 3, 4) are transmitted to the processing circuit T.

The emission spectrum from emitter E1 is located in the absorption band of a first gas to be detected and the emission spectrum of emitter E3 is located in the absorption band of the second gas to be detected. The emitter E2 is associated with emitter E1 to measure the concentration of the first gas and the emitter E4 is associated with the emitter E3 to measure the concentration of the second gas.

The device as shown in FIG. 3 comprises four emitters, and can be used to make a measurement of the concentration of two different gases (N1 and N2 respectively). More generally, the invention relates to a device comprising 2×n emitters to make a measurement of the concentration of n different gases.

Figure 4:
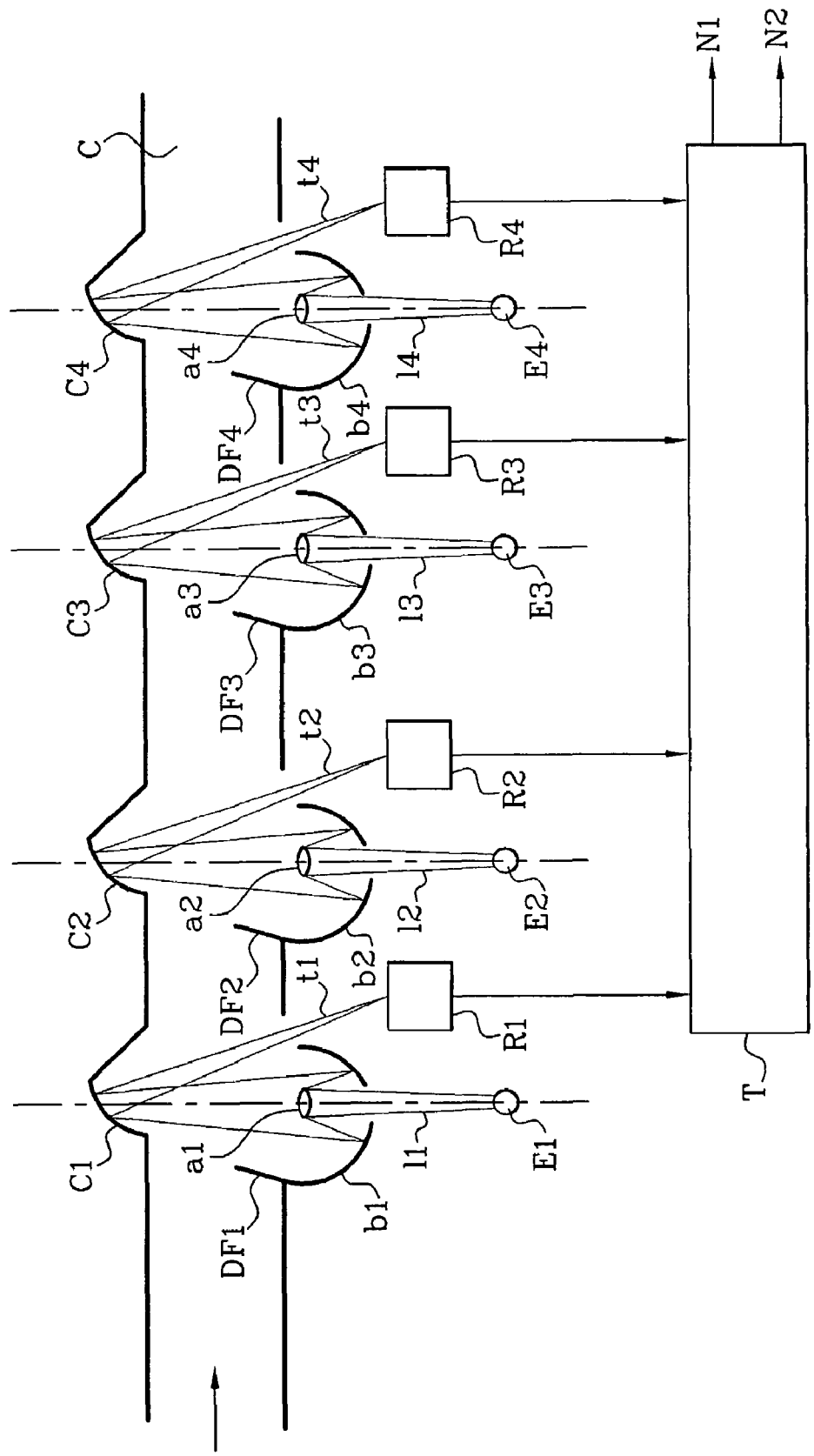
FIG. 4 shows a second example embodiment of a gas concentration measurement device according to the invention.

FIG. 4 shows a second example embodiment of a device for measuring the gas concentration according to the invention.

According to this second example, mirrors are used for the transmission of radiation in the cavity. The radiation li (i=1, 2, 3, 4) that enters the cavity is reflected by mirrors ai, bi and ci in sequence. Mirrors bi and ci are based on each side of the cavity C. The mirror ci is oriented so as to enable radiation ti to exit from the cavity through an orifice provided for this purpose. For example, mirrors can be made using folded and then polished metallic parts. This technology has the advantage that it can easily be used and it avoids the need for a ZnSe lens. Protection deflectors DFi can be used to overcome possible dirt accumulation of measurement systems by impurities carried by the gas flow. If they become dirty, the deflectors DFi can be cleaned using a high temperature heating device which burns off the impurities.

According to the example embodiment shown in FIG. 4, the emitters Ei (i=1, 2, 3, 4) and the reception means Ri are placed on the same side of the cavity. Advantageously, the processing electronics for emission and for reception of the radiation can then be placed at the same location. It is then easier to protect the optical emission and reception parts. Furthermore, the optical radiation path through the cavity is a forward-return type path. This path is then approximately twice as long as the path followed by the radiation in the previous cases (see FIGS. 1, 2 and 3). This can significantly improve the sensitivity of the measurement system.

Figure 5:
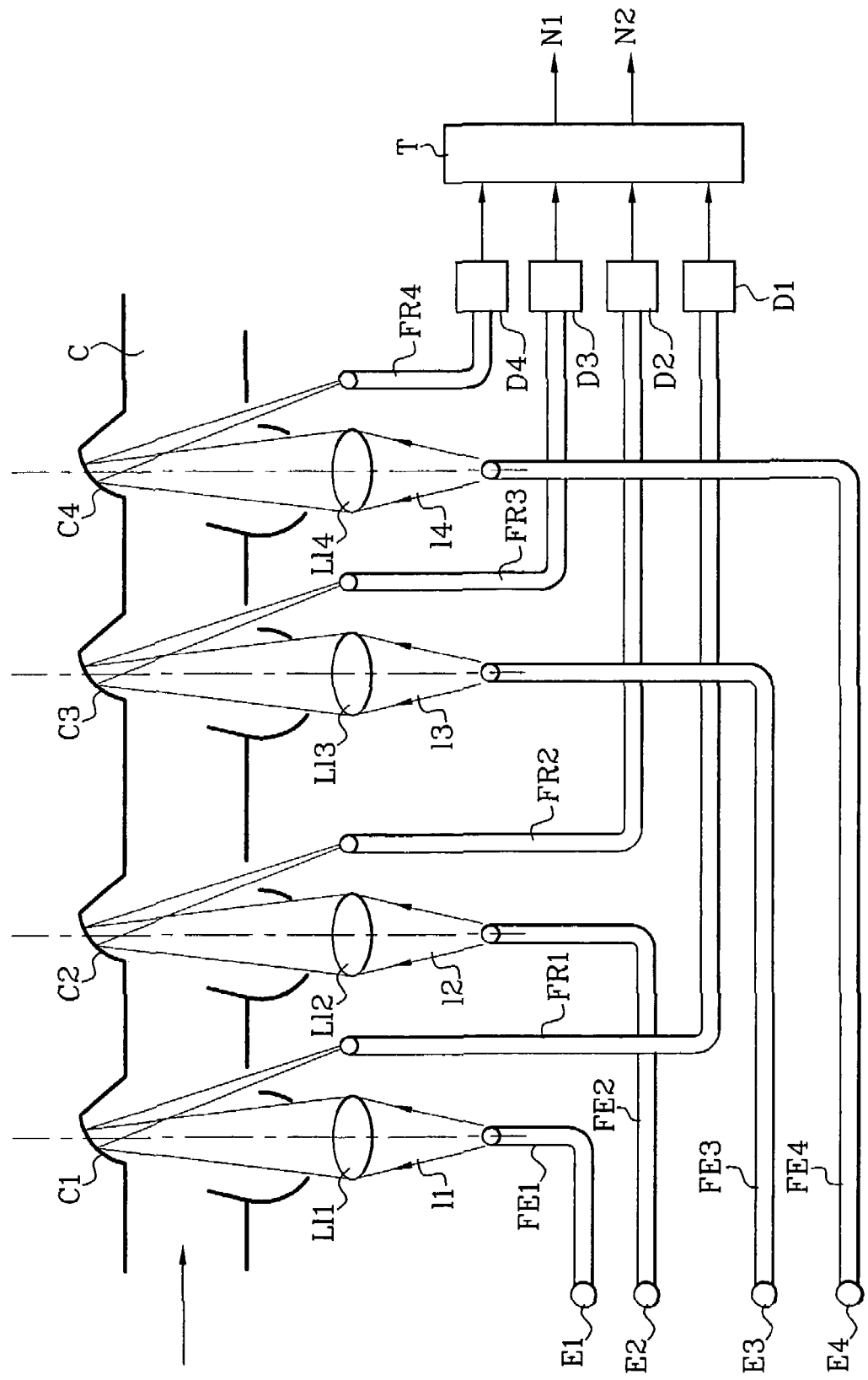
FIG. 5 shows a third example embodiment of a gas concentration measurement device according to the invention.

FIG. 5 shows a third example embodiment of the device for measuring the gas concentration according to the invention.

According to this third embodiment, light conductors are used to guide the various radiation li to the cavity C. Similarly, light conductors are used to guide the different radiation ti output from the cavity to the detection means. For example, the light conductors may be optical fibers or endoscopes.

Radiation li output from the emitter Ei (i=1, 2, 3, 4) is thus routed to the cavity C through a light conductor FEi and radiation ti output from the cavity is transmitted to the detector Di through a light conductor FRi. A lens Lli is used to focus radiation li in the cavity. The radiation that enters the cavity is reflected by a mirror ci. The mirror ci is oriented so as to enable the radiation ti to exit from the cavity through an orifice provided for this purpose.

One advantage of this embodiment is to enable the cavity C to be moved away from the optoelectronic processing zone. The temperature of the opto-electronic processing zone may then be made different from the temperature of the cavity (for example, the temperature may be lower). This advantage is particularly useful to analyze exhaust gases in an automobile.

Within the context of the invention described above, the emitters may be grouped on the same substrate in the form of a module or a matrix of emitters. The emitters are pumped by a network of laser diodes with a wavelength equal to approximately 800 nm. The dimensions of the network of laser diodes are approximately equal to the dimensions of the pump laser emitters. A module or a matrix is made after epitaxy and after the mirrors have been made, either by lithography and etching to clear emitting areas facing the active areas of the pump emitters, or by using a metallic mask to mask areas that must not emit light (with etched holes).

The embodiment of the invention shown in FIG. 5 comprises four emitters and is a means of making a measurement of the concentration of two different gases. The invention also relates to the case in which the device comprises 2×n emitters and can be used to make a measurement of the concentration of n different gases. Advantageously, the number n can be fairly high (for example equal to 10), due to the large choice of wavelengths within the 3 μm–6 μm range.

According to the embodiments of the invention described in FIGS. 3, 4 and 5, the measurement device includes one emitter for which the emission spectrum is outside the absorption band, for each gas for which the concentration is to be measured. However, the invention also relates to the case in which the number of emitters for which the emission spectrum is outside the gas absorption band is less than the number of gases for which the concentration is to be measured. For example, a single emitter with an emission spectrum outside the gas absorption band may be used to measure the concentrations of several different gases.

The invention claimed is:
1. A device for measuring a gas concentration, comprising:

a cavity (C) containing at least one gas for which the concentration is to be measured, at least one first emitter (E1) composed of an optical micro-cavity pumped by optical pumping means and for which the emission spectrum is within the gas absorption band, at least one second emitter (E2) composed of an optical micro-cavity pumped by optical pumping means and for which the emission spectrum is outside the gas absorption band, a reception means (Ri) for measuring the optical intensity (I) of a first radiation output from the first emitter (E1) and transmitted through the cavity (C), and the optical intensity ($I_0$) of a second radiation output from the second emitter (E2) and transmitted through the cavity (C), and a processing circuit (T) for measuring the gas concentration (N) starting from the optical intensity (I) of the first radiation and the optical intensity ($I_0$) of the second radiation.

2. The device according to claim 1, characterized in that it comprises a first optical element (Lli) located on a first wall of the cavity to enable the radiation (li) output from an emitter (Ei) to penetrate into the cavity (C) and a second optical element (Lti) located on a second wall of the cavity located facing the first wall to enable the radiation that penetrated into the cavity to leave the cavity (C).

3. The device according to claim 1, characterized in that the cavity (C) comprises a first opening to enable the radiation (li) output from an emitter (Ei) to penetrate into the cavity, in that the cavity includes a system of mirrors (ai, bi, ci) to propagate the radiation inside the cavity and in that the cavity comprises a second opening, close to the first opening, to enable the radiation propagated by the system of mirrors to leave the cavity (C).

4. The device according to claim 3, characterized in that the system of mirrors (ai, bi, ci) is configured such that the path of the radiation that penetrates inside the cavity is at least an approximately forward-return path between the first and the second opening.

5. The device according to claim 3, characterized in that the mirrors (ai, bi, ci) are folded and polished metallic parts.

6. The device according to claim 3, characterized in that it comprises a light conductor (FEi) to guide the radiation output from an emitter (Ei) to the first opening and a light conductor to guide the radiation output from the second opening to a reception means (Ri).

7. The device according to claim 6, characterized in that the light conductor is an optic fiber or an endoscope.

8. The device according to claim 5, characterized in that the emitters are grouped in the form of modules or matrices.

9. The device according to claim 1, characterized in that the optical pumping means are composed of laser diodes.

10. The device according to claim 1, characterized in that the reception means comprise a first reception means to measure the optical intensity of the first radiation (I) and a second reception means to measure the optical intensity of the second radiation ($I_0$).

11. The device according to claim 1, characterized in that the reception means comprise at least one reception means activated selectively to measure either the optical intensity of the first radiation (I), or the optical intensity of the second radiation ($I_0$).

12. The device according to claim 1, characterized in that the deflectors (DFi) are placed inside the cavity (C).

13. The device according to claim 1, characterized in that the optical micro-cavities of the first (E1) and/or second (E2) emitter comprise an active region manufactured from semiconducting materials such as CdHgTe, GaAlN, AlBN, GaAlAs, GaAsSb, GaAlSb, or with different families of semiconducting alloys in the II–VI family (compounds of Cd, Zn, Hg, Mn, Mg with Se, S, Te), or the III–V family (Ga, Al, In, B with N, As, P, Sb).

14. A device for checking the operation of a catalytic element in an exhaust line of an automobile vehicle, characterized in that it comprises a device according to any one of the above claims.

* * * * *